United States Patent [19]

Kang et al.

[11] 4,186,025

[45] Jan. 29, 1980

[54] AQUEOUS POLYSACCHARIDE COMPOSITION

[75] Inventors: Kenneth S. Kang, LaJolla; George T. Veeder, III; Danny D. Richey, both of San Diego, all of Calif.

[73] Assignee: Merck & Co., Inc., Rahway, N.J.

[21] Appl. No.: 864,298

[22] Filed: Dec. 27, 1977

Related U.S. Application Data

[60] Continuation-in-part of Ser. No. 768,517, Feb. 14, 1977, which is a continuation of Ser. No. 616,733, Sep. 25, 1975, abandoned, which is a division of Ser. No. 373,724, Jun. 26, 1973, Pat. No. 3,933,788, which is a continuation-in-part of Ser. No. 197,941, Nov. 4, 1971, abandoned.

[51] Int. Cl.$^2$ .......................... C08L 5/00; C09J 3/02; C09J 3/18

[52] U.S. Cl. .......................... 106/162; 8/62; 106/124; 106/208; 106/288 Q; 435/104; 435/852; 252/8.5 C; 252/8.55 D; 536/1

[58] Field of Search .......................... 616/733; 373/724; 197/941; 106/162, 208, 124; 536/1

[56] References Cited

U.S. PATENT DOCUMENTS

| | | | |
|---|---|---|---|
| 3,020,207 | 2/1962 | Patton | 195/31 P |
| 3,256,271 | 6/1966 | Schweiger | 195/31 P |
| 3,382,229 | 5/1968 | Patton | 536/1 |
| 3,729,460 | 4/1973 | Patton | 106/25 X |
| 3,894,976 | 7/1975 | Kang et al. | 260/17.4 ST |
| 3,933,788 | 1/1976 | Kang et al. | 260/209 |
| 3,960,736 | 6/1976 | Free et al. | 166/308 |
| 3,960,832 | 1/1976 | Kang et al. | 260/209 R |
| 4,073,653 | 2/1978 | Lindroth | 106/26 |

OTHER PUBLICATIONS

Kaneko et al., Chemical Abstracts, vol. 73, No. 75671lc, 1970.

Meisel-Mikolajczyk et al., Chemical Abstracts, No. 12393e, 1962.

Whistler, et al., Industrial Gums, 2nd Ed., Academic Press, N.Y. 1973.

*Primary Examiner*—Howard E. Schain
*Attorney, Agent, or Firm*—Gabriel Lopez; Hesna J. Pfeiffer; Julian S. Levitt

[57] ABSTRACT

A process for producing a heteropolysaccharide by a bacterial fermentation procedure in which a species of bacteria or a mutant thereof is incubated in a fermentation medium which contains a carbon source, preferably a hydrolyxed starch, a source of magnesium ions, a source of phosphorous, a source of nitrogen and water with the incubation taking place at a temperature of about 28° to about 35° C.

1 Claim, No Drawings

AQUEOUS POLYSACCHARIDE COMPOSITION

RELATED APPLICATIONS

This application is a continuation-in-part of application Ser. No. 768,517 filed Feb. 14, 1977 which is a continuation of application Ser. No. 616,733 filed Sept. 25, 1975, now abandoned, which is a division of application Ser. No. 373,724 filed June 26, 1973, now U.S. Pat. No. 3,933,788, issued Jan. 20, 1976 which is a continuation-in-part of application Ser. No. 197,941 filed Nov. 4, 1971, now abandoned.

DETAILED DESCRIPTION

It is known that heteropolysaccharides can be produced by certain microorganisms. Some of such heteropolysaccharides function as hydrophilic colloids and because of their viscosity properties and rheology have been used as thickening agents for aqueous systems. One known method of obtaining such heteropolysaccharides is by fermentation of an appropriate nutrient medium with certain Xanthomonas organisms. Cf. U.S. Pat. Nos. 3,020,207 and 3,256,271.

As with other fields of technology, research has continued with the objective of discovering new heteropolysaccharides having useful properties as thickening, suspending and/or stabilizing agents. It is an object of this invention to provide a method for making this new heteropolysaccharide having these desirable properties. It is another object to provide organisms for making this new compound. A still further object is the provision of a temperature sensitive, excess-iron requiring organism for making this new compound. Other objects of the invention will become evident from the ensuing description.

The present invention pertains to a novel heteropolysaccharide which is produced by the action of a bacteria on a selected carbon source. Further, the invention pertains to a novel process for producing a heteropolysaccharide by bacterial fermentation of a selected carbon source under controlled conditions. The heteropolysaccharide of this invention is a high molecular weight polysaccharide containing primarily carbohydrate residues and a minor amount of protein. It is sometimes referred to as a "gum", but it is believed that the heteropolysaccharide terminology is more accurate and precise. In the following description of our invention, it will sometimes be referred to as Heteropolysaccharide 10 or as Heteropolysaccharide S-10 under which designation it is described and claimed in U.S. Pat. No. 3,933,788.

This novel compound may be prepared by fermentation of a suitable nutrient medium with a strain of *Klebsiella pneumoniae* which does not grow at 37° C. in the absence of iron. A deposit of this organism was made with the American Type Culture Collection on Aug. 11, 1971 under Accession No. ATCC 21711. At the time of deposit, based upon classification tests in the 7th Edition of Bergey's Manual of Determinative Bacteriology (1959), the organism was identified as *Erwinia tahitica*. When the 8th Edition of this work appeared in 1974, however, a change in classification tests resulted in a change of identification of the organism from *Erwinia tahitica* to *Klebsiella pneumoniae*. A restricted deposit of a double-blocked mutant of this organism which requires iron, insufficient of which is available in the human body, for growth at 37° C. has been deposited with the American Type Culture Collection on July 25, 1977, under Accession No. ATCC 31311. Under the conditions of deposit, the mutant culture will be freely available to the public upon issuance of a United States patent on the present invention, and is to be released to any person authorized by the Commissioner of Patents and Trademarks to receive it under Rule 114 of the Rules of Practice in patent cases.

The bacterium identified as ATCC 21711 is a non-virulent strain of *Klebsiella pneumoniae* isolated from a Tahitian soil sample. *Klebsiella pneumoniae* is an ubiquituous organism found in water, soil, and all manner of vegetable matter. In addition, it is found in large numbers in industrial settings such as cooling tower water and paper mill effluents. In none of these situations is there evidence for *Klebsiella pneumoniae* causing any health problem. Soil isolates such as this are generally considered to be safe.

Thirty grams of the soil sample were added to 300 ml of sterile San Diego tap water to form a mixture which was placed on a reciprocating shaker. After mixing in this fashion for approximately 60 minutes, a loopful of the soil solution was streaked onto YM agar plates. The YM (Yeast Malt) agar was formed by adding to 1,000 ml of distilled water 41 gms. of a mixture containing 3 parts by weight of a yeast extract, 3 parts by weight of a malt extract, 5 parts by weight of a peptone and 10 parts by weight of dextrose (mixture supplied by Difco Laboratories, Inc., Detroit, Mich.) together with 20 parts by weight of agar. The YM agar plates were incubated at 30° C. for 48 hours. After incubation, the plates were examined and the slimy colonies were transferred to fresh YM agar plates. After further incubation for 48 hours at 30° C., the cultures were purified by subculturing onto YM agar plates. The purified cultures were finally transferred onto YM slants. The cultures may be maintained in the lyophilized state.

An air-dried film of a 24-hour old culture grown in E-1 medium was stained by the method of Gram (Manual of Microbiological Methods, Society of American Bacteriologists, McGraw Hill, New York, New York, 1957, page 16), and was found to be gram negative. The E-1 medium contained 5 gms of potassium acid phosphate, 0.1 gm of magnesium sulfate, 0.9 gms of ammonium nitrate, 0.5 gms of Promosoy 100 (an enzymatic digest of soybean meal sold by Central Soya Chemurgy Division), 30 gms of hydrolyzed starch and 1 liter of tap water. The hydrolyzed starch was obtained by heating Pearl starch (Staley Manufacturing Company) at a concentration of 30% by weight in water with an α-amylase enzyme (Tenase, supplied by Miles Laboratory) at a weight ratio of about 45 to 700 parts of starch for each part of the α-amylase enzyme. After addition of the α-amylase enzyme, the solution was incubated at 60° C. for two hours, then placed in a boiling-water bath for 30 minutes or autoclaved for 15 minutes at 15 psi at a temperature of 120° C. The pH of the E-1 medium was about 7.6 to 7.8.

The cells of the bacteria are non-motile, non-sporeforming rods having a size range of 0.75–1.0 by 1.0–2.0 microns. The organism usually occurs as single cells and only rarely forms chains. The bacterium is heavily encapsulated and also produces a large amount of extracellular slime in the E-1 medium, as described previously.

The bacteria were observed by electron microscopic examination at a magnification of about 161,000 times. In observing the bacteria under the electron microscope, it was observed by three different methods, i.e., phosphotungstic acid negative staining, uranyl acetate negative staining and platinum-carbon shadowing. These methods are described in "Techniques for Electron Microscopy", Second Edition, edited by D. H. Kay, Blackwell Scientific Publications, Oxford, England (1965). As observed, the bacteria did not possess flagella.

The colonial morphology of the bacteria was observed by growing the bacteria in three different media. On a nutrient agar plate, the organism forms circular, convex, entire, smooth, opaque white-to-cream colored colonies. The colonial morphology on YM agar is the same as on the nutrient agar plate, but more copious growth is usually evident. On Levine's EMB agar, the bacteria formed heavily mucoid colonies. On a nutrient agar slant, the growth is heavy, moderately viscid, creamy and filiform. The organism exhibits a large amount of sub-surface growth in Nutrient Broth with a heavy flocculent sediment. There was no surface growth. The organism did not grow at a temperature of 4° C. on YM agar after two weeks of incubation, but grew very well in this medium at room temperature (22°–24° C.). The organism also grows well at 30° C. and at 35° C. on YM agar but will not grow at a temperature of 55° C. The optimum growth temperature appears to be about 28° to about 35° C. and the thermal death point of the bacteria is about 55° to 60° C.

The Nutrient Broth contained 0.3% by weight of beef extract and 0.5% by weight of peptone is distilled water. The nutrient agar was composed of Nutrient Broth in admixture with about 1.5% by weight of agar.

The bacteria were also grown in litmus milk using the procedure described at page 40 of "Laboratory Methods in Microbiology", by W. F. Harrigan and M. E. McCance, Academic Press, New York, New York, (1966). The bacteria produced an acid reaction in litmus milk after 24 hours, and formation of an acid curd with peptonization and reduction of the litmus were observed after 96 hours.

The optimum pH conditions for growth of the bacteria were determined in E-1 medium, as described previously. It is found that the optimum pH for growth of the bacteria was about 7.0±0.5.

Antibiotic sensitivity tests were run on the bacteria using a paper disc method. In this procedure, paper discs, having a diameter of 5 or 6 millimeters were cut from filter paper and autoclaved to kill any organisms thereon. The autoclaved filter paper was then soaked in a dilute aqueous solution of the antibiotic under test and the impregnated paper disc was placed on the center of a lawn of bacteria in a petri disch and incubated under aerobic conditions for 30 hours at 30° C. The lawn of bacteria was prepared by first heating YM agar growth medium, as defined previously, to about 100° C. on a water bath to melt it. The liquified agar was then cooled to 45° C. and poured into a sterile petri dish. The agar was then solidified by cooling to room temperature. After solidification, one-tenth milliliter of a suspension of the bacteria was smeared evenly across the surface with a sterile glass rod. There was obtained, on incubation, a hazy, homogeneous-appearing bacterial growth. The term "lawn" refers to such a preparation which contains a very high bacterial count.

After incubation of the solidified agar at 30° C. for about 24 hours in the petri dish in contact with the impregnated disc, as described above, the bacterial growth was observed. If the bacteria were sensitive to the antibiotic, there was a clear area around the periphery of the disc which was free from bacteria. The determination of antibiotic sensitivity by the above method is described in the literature at pages 206–212 of "Diagnostic Bacteriology" by I. G. Schaub et al., 5th Ed., the C. V. Mosby Co., St Louis, Mo.).

When tested in the above manner, it was found that the bacteria were resistant to penicillin at a disc concentration of 0.5 units of penicillin and resistant to novobiocin at a disc concentration of 2.5 micrograms. The bacteria were found to be sensitive to streptomycin at a disc concentration of 1.5 micrograms, sensitive to neomycin at a disc concentration of 1.5 micrograms and sensitive to polymyxin-B at a disc concentration of 1.3 micrograms. In further tests, the biochemical characteristics of the bacteria were determined. The bacteria tested negative to the Methyl Red test procedure described at page 60 of the Harrigan and McCance text, supra. The bacteria gave a positive catalase test, a positive urease test, and a weakly positive amylase test. The catalase, urease and amylase tests are set forth, respectively, at pages 65, 56, 65 and 58 of the Harrigan and McCance text, supra. The bacteria also gave a positive arginase test after five days at aerobic conditions according to the method of M. J. Thornley "Journal of Applied Bacteriology", Vol. 23, page 37 (1960). The bacteria gave a negative indole formation test, a negative gelatin liquefaction test, a positive hydrogen sulfide formation test by the lead acetate procedure, a positive citrate utilization test and a positive acetylmethyl carbinol formation test. The indole formation, gelatin liquefaction, nitrate reduction, citrate utilization, acetylmethyl carbinol formation, and the lead acetate hydrogen sulfide tests are set forth, respectively, at pages 53, 51 and 52, 56 and 57, 61, 60 and 55 of the Harrigan and McCance text, supra.

Subsequent hydrogen sulfide formation tests using the more sensitive triple sugar iron agar assay indicated that this organism actually does not form hydrogen sulfide. The hydrogen sulfide formation test using triple sugar iron agar is set forth at pages 54–55 of the Manual of Microbiological Methods, Society of American Bacteriologists, McGraw-Hill, New York 1957.

The bacterium was found to be fermentative when tested by the Hugh Liefson Glucose test as described at page 59 of the Harrigan and McCance text, supra. The bacteria tested positive in malonate broth according to the procedure described on pages 227–228 of the publication entitled "A guide to the Identification of the Genera of Bacteria" by F. B. D. Skerman, Williams and Wilkins Company, Baltimore, (1967). Lysine decarboxylase and cytochrome oxidase activity were determiend using Patho Tec test papers from General Diagnostics Division of Warner-Chilcott Laboratories. The bacteria tested positive to lysine decarboxylase and negative to cytochrome oxidase.

The organism was tested to determine its tolerance to salt. It grew within 24 hours in nutrient broth containing 5% by weight of sodium chloride when incubated under aerobic conditions at 30° C. When incubated under the same conditions in nutrient broth containing 7% by weight of sodium chloride, the organism grew within 48 to 72 hours.

In a further series of experiments, the bacteria were grown in various basal media containing a carbohydrate source. The growth of the bacteria was observed to determine whether the bacteria caused fermentation with production of acid and gas, caused fermentation with production of acid only, or caused no fermentation. In conducting these experiments, the basal medium described by D. W. Dye, "New Zealand Journal of Science", Vol. 5, pages 393–416 (1962), was first sterilized by autoclaving. A carbohydrate solution was then made up and was sterilized by filtration through a Seitz Filter Pad in which the holes passing through the filter pad are approximately 1/50th micron in diameter. No living bacteria is sufficiently small to permit its passage through the above-described Seitz Filter pad. Thus filtration in this manner is a convenient way to sterilize an aqueous media without the use of heat.

The sterilized carbohydrate solution was then added to a heat sterilized basal medium as described by Dye in a sufficient amount to give a total carbohydrate concentration of 0.5% by weight. The pH of the basal medium was about 7 and contained a few drops of Brom-Cresol Purple, which was used as the pH indicator. Following this, the liquid growth medium was inoculated with bacteria, the test tube was closed, and the organism was incubated at a temperature of 30° C. The results of these tests are shown in the following Table.

TABLE

| Fermentation with production of acid and gas | Fermentation with production of acid only | Not Fermented |
|---|---|---|
| D-Arabinose | Dextrin | Adonitol |
| D-Cellobiose | | Dulcitol |
| D-Fructose | | Inulin |
| D-Galactose | | Sodium Alginate |
| D-Glucose | | Starch |
| Inositol | | |
| D-Lactose | | |
| D-Maltose | | |
| Mannitol | | |
| D-Mannose | | |
| D-Raffinose | | |
| L-Rhamnose | | |
| D-Ribose | | |
| Salicin | | |
| D-Sucrose | | |
| D-Trehalose | | |
| D-Xylose | | |

As shown in the above Table, the bacteria were able to utilize a wide variety of carbohydrates for growth. The pH indicator, Brom-Cresol Purple, gives a yellow coloration at an acid pH of less than 5.2. In the above tests, control tests were carried out under the same conditions with the same media without the presence of the bacteria. The control test showed no change in the pH during incubation; thus, indicating that the resultant pH change was caused by the bacteria.

When the organism was grown in E-1 medium containing glucose, a yellowish pigmentation was noted. A procedure for the extraction of carotenoid pigments was followed and the results indicated that the yellowish pigment is not carotinoid. The clear supernatant medium remaining after removal of the cells was yellow which indicated that the yellow pigment produced by the organism is water soluble.

On the basis of the above tests, it was attempted to identify the bacteria in terms of morphological characteristics and physiological properties, as compared with those of known organisms recorded in the "Bergey's Manual of Determinative Bacteriology", reprint of 7th Edition, Williams and Wilkins Company, Baltimore Md. (1959). On the basis of the accumulated information, the organism was believed to belong to the family "Enterobacteriaceae". This conclusion was based on the fact that the organism is a gram negative, non-sporeforming, straight rod which produces acid and gas from glucose. The fact that the organism ferments lactose within 48 hours and does not produce the pigment prodigiosin apparently limited it to two tribes: Escherichieae and Erwinieae. The ability of the organism to produce hydrogen sulfide as well as an acid curd in litmus milk with peptonization and reduction of the litmus, indicated that the organism did not belong to the tribe Eschericheieae.

The biochemical characteristics of this organism are similar to those of *Klebsiella pneumoniae, Erwinia nimipressuralis* and *Erwinia dissolvens* in the 7th Edition of Bergey's Manual. Because of the litmus milk reaction and pigment production by this organism, it was originally concluded that it was a new species of Erwinia. However, when the 8th edition of Bergey's Manual was published, it contained a new description for the genus Erwinia within which this organism would not fit. Accordingly, after exhaustive testing both Erwinia dissolvens and *E. nimipressuralis* were dropped from the genus Erwinia and it was concluded that they belonged to Klebsiella and Enterobacter, respectively. Further, more definitive studies on $H_2S$ production by this organism showed that although $H_2S$ produced as indicated by positive results in very sensitive tests, it is not produced in medium designed for this test on this family of microorganisms. Based on these results and on the current taxonomical status of the family Enterobacteriaceae, it is now believed that this organism is a strain of *Klebsiella pneumoniae*.

The properties of our *Klebsiella pneumoniae* bacteria are for convenience summarized below:

Morphology a. Cells—Gram negative, non-motile, non-spore forming rods having a size range of $0.75-1.0 \times 1.0-2.0$ microns. Bacteria is encapsulated and produces a large amount of extracellular slime. Bacteria does not possess flagella and usually occurs as single cells and only rarely forms chains.

b. Colony—Nutrient agar plate: Forms circular, convex, entire, smooth, opaque, white-to-cream-colored colonies.

YM Agar—Same characteristics as observed on nutrient agar plate but copious growth is usually evident.

Levine's EMB Agar—The bacteria have a heavy mucoid colony type.

Growth Characteristics a. Nutrient agar slant—Heavy, moderately viscid, creamy and filiform.

b. Nutrient broth—Exhibits a large amount of subsurface growth with a heavy flocculent sediment. There is no surface growth.

c. Litmus milk—Produced acid reaction after 24 hours and formation of acid curd with peptonization and reduction of the litmus after 96 hours.

d. Growth Temperature—Optimum growth temperature of about 28° to about 35° C. and thermal death point of about 55°–60° C.

e. Growth pH—Optimum pH is $7.0 \pm 0.5$.

Salt Tolerance

Organism will grow under aerobic conditions at 30° C. in nutrient broth containing 5% by weight of NaCl within 24 hours incubation and containing 7% by weight of NaCl within 48 to 72 hours of incubation.

Antibiotic Sensitivity

Penicillin—Resistant

Novobiocin—Resistant
Streptomycin—Sensitive
Polymyxin-B—Sensitive
Neomycin—Sensitive
Biochemical Characteristics
  Methyl Red—Negative
  Catalase—Positive
  Urease—Positive
  Oxidase—Negative
  Amylase—Weakly Positive
  Cellulase—Positive
  Arginase—Positive
  Indole Formation—Negative
  Hydrogen Sulfide formation—Negative
  Citrate utilization—Positive
  Acetylmethyl carbinol formation—Positive
  Gelatin Liquefaction—Negative
  Hugh Liefson Glucose test—Fermentative
  Malonate broth—Positive
  Lysine decarboxylase—Positive
  Cytochrome oxidase—Negative Isolation of S-10 Mutant Fer-1

Strain Fer-1, the excess iron-requiring temperature sensitive mutant was isolated from temperature sensitive mutant ts-856 which in turn was isolated from strain. PRM-3, which was isolated from strain PRM-2, which was isolated from PRM-1, which was isolated from S-10, the original bacterium isolated from the Tahitian soil sample. Thus, the pedigree goes as follow: S-10→PRM-1→PRM-2→PRM-3→ts-856→Fer-1.

PRM-1 was isolated from S-10 by selection for resistance to phage 1 that attacked S-10. A culture containing about $10^7$ bacteria/ml was mixed with excess phage for five hours, then plated on nutrient agar. One of the colonies that grew in the presence of phage was selected as PRM-1. In a similar manner PRM-2 was selected as a strain resistant to phage 2 and PRM-3 was selected as a strain resistant to phage 3. Phages 1, 2 and 3 were strains isolated in our laboratory.

Strain ts-856 was isolated from PRM-3 in the following manner. A 24-hour culture of PRM-3 was resuspended in citrate buffer pH 5.5 (0.1 M sodium citrate, 10.5 g citric acid, 4.4 g NaOH, diluted to 500 ml and pH adjusted to 5.5) and treated with N-methyl-N-nitroso-N'-nitroguanidine (NTG) at a concentration of 250 μg/ml at 37° C. for 30 minutes. A 0.1 ml aliquot was grown overnight in 10 ml nutrient broth. A 1 ml sample was removed, diluted to 5 ml and treated with 10,000 units/ml of penicillin at 37° C. for 2½ hours. Excess penicillinase was added and the suspension cooled to 30° C. The culture was plated for single colonies then replica plated at 30° and 37° C. on nutrient agar. The mutant ts-856 was a strain that grew at 30° C. but did not grow at 37° C.

Strain Fer-1 was selected from ts-856 in the following manner. A 24-hour culture was re-suspended in citrate buffer at pH 5.5 and treated for two hours with 250 μg/ml NTG. An aliquot was diluted (0.1 ml into 10 ml) and this allowed to grow overnight in nutrient broth. The culture was then plated for single colonies on nutrient agar. This plate was replica plated to nutrient agar and McConkey agar+200 μg/ml Bacitracin plates which were incubated at 30° C. The mutant Fer-1 was a strain that did not grow on McConkey agar Bacitracin plates but grew on nutrient agar at 30° C. The mutant may be frozen or lyophilized in conventional manner for storage. Lyophilization is preferred.

The heteropolysaccharide produced by *Klebsiella pneumoniae* Fer-1, ATCC 31311, is identical in all respects to the heteropolysaccharide produced by the parent organism, *Klebsiella pneumoniae*, ATCC 21711.

In practicing our invention, a suitable nutrient fermentation medium is inoculated with a heteropolysaccharide saccharide producing strain of Klebsiella pneumoniae and permitted to incubate at a temperature of about 33 to about about 37° C., preferably about 35° C., or in the case of the mutant at a temperature of about 28 to about 32° C., preferably about 30° C., for a period of about 45 to about 60 hours. The bacteria are quite fastidious in their nutritional characteristics in that they require a fairly specific carbon source in order to produce massive amounts of the heteropolysaccharide. The carbon source required by the bacteria in order to produce the polysaccharide is an oligosaccharide containing from about 3 to about 10 monomer units at a concentration of about 1 to about 5% by weight, and preferably about 2 to 4% by weight.

A further ingredient which is present in the fermentation medium is a source of magnesium ions. The magnesium salt content of the fermentation medium may range from about 0.005 to about 0.02% by weight. Suitable sources of magnesium ions include water soluble magnesium salts, such as magnesium sulfate heptahydrate, magnesium acetate, magnesium chloride, magnesium nitrate and magnesium acid phosphate which may be deliberately added or present as an impurity in the carbon source or the water used.

The pH of the fermentation medium is important to suitable growth of the bacteria. We have found that the optimum pH for production of Heteropolysaccharide-10 is in the range of about 6.0 to 7.5, and preferably about 6.0 to 6.5. Control of the pH can generally be obtained by the use of a buffer compound such as dipotassium acid phosphate at a concentration from about 0.4 to about 0.6% by weight of the fermentation medium. Any of the various sodium and potassium salts of phosphoric acid may be used as buffer, e.g. $KH_2PO_4$, $K_2HPO_4$, $K_3PO_4$, $NaH_2PO_4$, $Na_2HPO_4$, or $Na_3PO_4$. When the pH is adjusted to about 7, there will be present about equal amounts of mono- and dibasic phosphates.

Conversely, the pH can be controlled through conventional means by using a pH meter coupled with a source of a suitable base, e.g. an alkali metal hydroxide, such as a solution of potassium or sodium hydroxide. As the pH is lowered due to the production of acids during the fermentation reaction, small quantities of the potassium or sodium hydroxide solution may be automatically added by the pH controller to keep the pH within the desired range. For best results it is desired that some dipotassium acid phosphate be present because of its buffer action, but the amount can be less, i.e. 0.05–0.15% by weight, when an alkali metal hydroxide is also used. In a system where pH is controlled by alkali addition, the preferred range is 6.0–6.5. If it rises above 6.5, an acid such as sulfuric acid may be added to reduce it to the desired range.

Generally, the bacterial fermentation process of our invention does not require the addition of alkali to control the pH during the fermentation. The pH of the fermentation beer drops to about 6.0 which generally occurs after 10 to 20 hours of fermentation, then increases to about 6.5–6.8, and generally remains at this level for the balance of the fermentation. If the pH drops after about 30–50 hours, potassium hydroxide or another suitable base, such as sodium hydroxide, may be added to maintain the pH at at least about 6.5.

At least a trace quantity of phosphorus, generally in the form of a soluble potassium salt, is also present in the fermentation medium. Larger quantities of phosphorus, such as about 0.65% by weight (calculated as dipotassium-acid-phosphate) of the fermentation medium, can, however, also be used.

In order to obtain a rapid fermentation, we have found that it is essential to have a sufficient quantity of oxygen available for the growing *Klebsiella pneumoniae* culture or mutant thereof. If either too much or too little oxygen is available, the production of Heteropolysaccharide 10 by the bacterial culture is slowed down. Our process requires that sufficient oxygen be made available for the bacteria. The oxygen requirements can be defined in terms of a sulfite oxidation value, which is a measure of the rate of oxygen uptake in the fermentor under the agitation and aeration conditions employed. It is, however, preferred to describe this aspect of the process in terms of dissolved oxygen, and in this regard it is important that a dissolved oxygen level of 5–10% be maintained at least during the first 20–40 hours of the fermentation. Thus, the liquid medium should contain 5–10% of the amount of oxygen that can be dissolved in the medium, when the oxygen is added as air.

A source of nitrogen is also present in the fermentation medium. The nitrogen source may be organic in nature as, for example, soy protein; an enzymatic digest of soybean meal such as Soy Peptone, Type-T; Promosoy 100; a pancreatic hydrolysate of casein, such as N-Z amine Type A; an enzymatic digest of proteins, such as Ferm Amine Type IV, or distillers solubles, such as Stimuflav. Soy protein is sold by Nutritional Biochemical Corp., Cleveland, OH; Promosoy 100 is sold by Central Soya Chemurgy Division; Stimuflav is marketed by Hiram Walker & Sons, Inc., and the other materials are sold by Sheffield Chemical, Norwich, New York. When utilizing an organic nitrogen source in the fermentation medium, an amount ranging between about 0.01 and 0.07% by weight of the fermentation medium is satisfactory.

Also, if desired, an inorganic nitrogen source, such as ammonium nitrate, ammonium chloride, ammonium sulfate, ammonium citrate or ammonium acetate may be present in the fermentation medium. The amount of such a salt which may be employed can range from about 0.02 to about 0.15% by weight and preferably from about 0.045 to about 0.1% by weight of the fermentation medium.

As described previously, the *Klebsiella pneumoniae* bacteria or mutant thereof are quite selective in their utilization of carbon sources with regard to the preparation of Heteropolysaccharich-10. The carbon source which we have found most suitable, and which is preferred in practicing the process aspect of our invention is starch that has been hydrolyzed with an α-amylase enzyme followed by heating at an elevated temperature. The type of starch used is not critical. Representative examples of starches that may be employed are corn starch—which is preferred, wheat starch, rice starch, potato starch and tapioca starch. Also acceptable are the commerical corn syrups which are starch hydrolysates.

Starch hydrolysates may be defined in terms of Dextrose Equivalent which is determined by the formula:

$$\text{Dextrose Equivalent} = \frac{\text{Reducing Sugar Concentration (\%)}}{\text{Starch Concentration (\%)}} \times 100$$

where the reducing sugar activity is determined as described by Lane and Eynon, Chemistry and Industry, p23 (1923) using the Soxhlet modification of Fehling's solution.

We prefer that the hydrolyzed starch used as a carbon source for producing Heteropolysaccharide-10 via the growth of *Klebsiella pneumoniae* or mutant thereof have a Dextrose Equivalent of about 20–30, and preferably about 22–27. With commercial corn syrups, such as American Maize Lodex, the preferred Dextrose Equivalent is close to 30, and may be as high as about 35.

The starch hydrolysates used in our invention are readily prepared by methods known to those skilled in this art. For instance, a 30% aqueous corn starch solution containing 1.25–2.0% for weight of an α-amylase enzyme based on weight of starch (Tenase, Miles Laboratories) gave a starch hydrolysate having a Dextrose Equivalent of 19–20 when the temperature of the solution was raised from room temperature to 100° C. over a period of 5–15 minutes.

If the starch fractions in the hydrolysate were uniform in molecular weight, the degree of polymerization would be about 3–10 monomer units. In a typical preparation, a 30% aqueous corn starch solution containing 3.3% by weight of the starch of Tenase α-amylase enzyme was incubated at 60° C. for two hours and then boiled for 30 minutes. It had a Dextrose Equivalent of 20.

On completion of the fermentation, the desired Heteropolysaccharide-10 may be recovered by treatment of the fermentation beer with a miscible solvent which is a poor solvent for the heteropolysaccharide and does not react with it. In this way the heteropolysaccharide is precipitated from solution. The quantity of solvent employed generally ranges from about 2 to about 3 volumes per volume of fermentation beer. Among the various solvents which may be employed are acetone and lower alkanols such as methanol, ethanol, isopropanol, n-butanol, sec-butanol, tertiary butanol, isobutanol, and n-amyl alcohol. Isopropanol is preferred. Precipitation of the desired heteropolysaccharide is facilitated when the fermentation beer is first heated to a temperature of about 70 to about 90° C. for a short time, e.g. about 5 to 10 minutes, and then cooled to about 30° C. or lower before addition of the solvent. Thus, this is a preferred method of precipitating the heteropolysaccharide from the fermentation beer. The solid is recovered by separating it from the liquid, as by filtering or straining, and then drying at elevated temperature.

Heteropolysaccharide-10, produced according to the process of the present invention, is a high molecular weight product containing about 97% carbohydrate and 3% protein. It has an acetyl content of about 4.5%. The protein portion is represented by approximately 6 compounds which can be stained ninhydrin. The carbohydrate portion of the heteropolysaccharide consists of about 19% uronic acid, about 39% glucose, about 29% galactose and about 13% fucose. The approximate molar ratio of the glucose, galactose, uronic acid and fucose is 3:2:1.5:1, respectively. Heteropolysaccharide-10 has a specific rotation of $[\alpha]_D = +106°$ (c 0.25, water). It is essentially insoluble in dimethyl sulfoxide. It is only slightly soluble in acetone and lower alkanols.

The acetyl content of 4.5% is determined by treating a 0.1% aqueous solution in an oxygen-free atmosphere with a known volume of 0.01 N potassium hydroxide containing 1% (W/V) potassium chloride at room temperature. Aliquots are removed at elapsed time intervals and the acetyl content determined by back-titration with 0.01 N sulfuric acid.

The composition of the carbohydrate portion of Heteropolysaccharide-10 is determined by dissolving 0.5 grams of the product in 100 ml of water. 100 Ml of 4 N sulfuric acid is added to the resulting solution, and the mixture refluxed for 12 hours. The resulting solution is cooled and brought to pH 5–6 with barium carbonate. The resulting precipitate of barium sulfate is separated by filtration and barium ions removed from the filtrate using a cation exchange resin on the hydrogen cycle. After removal of the resin, the solution is concentrated to a syrup under reduced pressure at 35° C., and the sugars are tentatively identified by paper chromatography.

60 Mg of the above hydrolysate syrup is dissolved in 10 ml of water and the sugar is reduced by treating with 150 mg. of sodium borohydride for 12 hours. After decomposition of excess sodium borohydride by treatment with Amberlite IR-120 on the hydrogen cycle, the residual boric acid is removed by co-distilling several times with methanol. The resulting alditols are acetylated by treating with 5 ml of acetic anhydride in 5 ml of pyridine for 12 hours. Water is then added to the reaction mixture which is then concentrated to a small volume and co-distilled several times with chloroform. The resulting residue is dissolved in chloroform and gas liquid chromatography performed with a Hewlett-Packard Model 5750 chromatograph using 3% by weight of ECNSS-M on 80/100 Gas Chrom Q at 185° C. The sugars are identified by comparison with authentic standards and the proportions of alditol acetates determined directly from the peak areas on the gas chromatogram by integration.

The various components of the heteropolysaccharide were also characterized by the use of paper chromatography. The carbohydrate components were identified using descending paper chromatography on Whatman filter paper No. 4 using as solvents a butanol-acetic acid-water mixture (having a volume ratio of 6:1.5:2.5), a butanol-pyridine-water mixture (having a volume ratio of 4:4:2) and an isopropanol-pyridine-water mixture at a volume ratio of the components of 6:2:2. The chromatograms were stained using the aniline reagent as described at page 152 of "Chromatographic and Electrophoretic Techniques" by I. Smith, William Heinemann Medical Books, Ltd., and Interscience Publishers, Inc., New York, New York (1960). The other components in the heteropolysaccharide were characterized by using the butanol-acetic acid-water solvent mixture followed by staining of the chromatograms using the Bromocresol Green reagent and the ninhydrin reagent as described at pages 279, 95 and 96 of "Chromatographic and Electrophoretic Techniques", supra.

On the basis of the above determination, the major carbohydrate portion of the heteropolysaccharide is composed of glucose and galactose. A spot which migrated with an Rg value of 11–12 in the n-butanol-pyridine-water solvent system using the descending techniques was identified as a uronic acid by its staining characteristics with the naphtoresorcinol reagent. Another compound which had an Rf value of 69–73 in the butanol-acetic acid-water solvent by the ascending technique stained yellow with the bromocresol green stain and was ninhydrin negative. This compound is suspected to be an organic acid.

In typical chromatogram of the ninhydrin positive compounds, the lower four ninhydrin compounds stained blue or basic with the bromocresol green stain indicating that they are basic aminoacids. Two basic amino acids (lysine and arginine) were cochromatographed with the heteropolysaccharide hydrolysate and show migration patterns similar to two of the ninhydrin positive compounds in the hydrolysate.

The uronic acid content of the heteropolysaccharide was determined by decarboxylation with 19% hydrochloric acid. The liberated carbon dioxide was trapped in standard sodium hydroxide and determined by back-titration. From these results the uronic acid content was calculated. The uronic acid content of the heteropolysaccharide was also assayed by dissolving 2 grams of the purified material in 400 milliliters of distilled water. This solution was then stirred for 2 hours with 25 milliliters (packed volume) of H+- charged Amberlite 120 ion exchange resin. The resin was then removed by centrifugation and the solution was dialyzed overnight against distilled water and then for 3 hours against double distilled water. The volume of the heteropolysaccharide solution was then condensed to 420 milliliters using a Buchler Flash Evaporator. A 100 milliliter aliquot was titrated with 0.0492 Normal sodium hydroxide. The amount of uronic acid present in the heteropolysaccharide is then calculated through the use of a titration curve.

An infrared spectrum of the Heteropolysaccharide-10 was made on a dried thin film of the material using a Perkin-Elmer Model 337 Grating Infrared Spectrophotometer. The heteropolysaccharide evidenced two peaks at frequencies of 1720 and 1610 cm$^{-1}$ which indicate the presence of acetate and carboxylic groups, respectively. The peak at 1610 cm$^{-1}$ confirms the presence of a uronic acid. The product also shows a peak at 1400 cm$^{-1}$ indicating the presence of peptide bonds.

Heteropolysaccharide-10 is compatible with cationic dyes such as Methylene Blue-chloride and Alcian Blue (i.e., the cationic dye did not precipitate the heteropolysaccharide from solution).

As will be seen from certain of the following examples, Heteropolysaccharide-10 imparts viscosity to an aqueous medium when dissolved in water in low concentration. Because of this, its sensitivity to shear, its pseudoplasticity, its stability with salts, and because of its overall rheology, Heteropolysaccharide-10 is useful as a thickening, suspending and stabilizing agent in aqueous systems. More specifically, it is useful as an additive to textile printing pastes or in formulating low drift aqueous herbicidal compositions. It is also of value as a thickening or suspending agent in salad dressings, in forming thickened puddings, and as a thickener in adhesive compositions.

Heteropolysaccharide-10 is of particular value as an additive in aqueous paints because of its ability to improve the flow and leveling of such paints, and because of its pseudoplasticity. The paint may, of course, contain other ingredients in addition to the pigment, binders and colors, such as extenders, preservatives, dispersants, wetting agents, freeze-thaw stabilizers and the like, all of which are well-known to those skilled in the art, as are the methods used in preparing the heteropolysaccharide-containing paint.

Heteropolysaccharide-10 is also useful as a fluid loss control agent in drilling muds, completion fluids and similar aqueous media from which fluid losses to subterranean strata have to be controlled. In water flooding compositions, it is used as a thickening agent to impart sufficient viscosity to the aqueous medium so that the crude oil may be effectively displaced from the reservoir. In drilling muds and in waterflooding operations there will normally be present other materials such as weighting agents and metal salts.

In all of these applications, the heteropolysaccharide is added in low concentration, i.e. from about 0.3%–3.0% by weight, using mixing and formulating techniques well known to those skilled in the particular art. The viscosity of the composition may be varied as desired by adjusting the amount of Heteropolysaccharide-10 employed.

The following examples are given for the purpose of illustrating aspects of our invention, but are not to be construed as limiting.

EXAMPLE 1

A series of experiments were conducted to determine the effect of using various carbon sources in the bacterial fermentation on the yield of Heteropolysaccharide-10. The seed for the experiments was obtained by growing *Klebsiella pneumoniae*, ATCC 21711 for 24 hours in E-1 medium containing 3% by weight of hydrolyzed starch as the carbon source. The seed was then transferred aseptically to sterilized shake flasks containing 90 milliliters of basal E-1 medium and 10 milliliters of a 30% by weight aqueous solution of the carbon source under test. The quantity of the seed inoculum was 1% by weight of the total weight of the medium. After inoculation of the flasks, the mixture was incubated under aerobic conditions at 30° C. on a rotary shaker having a controllable speed range of 160 to 400 rpm. The results of these tests are set forth in the following Table I.

TABLE I

| Carbon Source (3%) | Ferm. Time (hrs.) | Final pH | Final Beer Viscosity (cps) |
|---|---|---|---|
| Glucose | 43 hrs. | 3.45 | 5 |
| Hydrolyzed Starch | 72 hrs. | 7.00 | 4,600 |
| Sucrose | 72 hrs. | 4.40 | 50 |
| Dextrin-1 | 72 hrs. | 7.50 | 0 |
| Maltose | 72 hrs. | 6.70 | 50 |

As shown in the above Table, the results of the fermentation vary greatly depending upon the carbon source which was employed. The use of hydrolyzed starch as the carbon source produced a satisfactory yield (1.61%) of the heteropolysaccharide as evidenced by the high viscosity of the fermentation beer. However, the use of glucose or dextrin-1 as the carbon source produced essentially no heteropolysaccharide. Similar results are obtained with *Klebsiella pneumoniae* Fer-1, ATCC 31311.

EXAMPLE II

In a further series of experiments which were conducted under the same conditions as set forth in Example I, various mixed carbon sources were employed to determine their effect on the production of the Heteropolysaccharide-10 by the *Klebsiella pneumoniae* bacterium. The results of these tests are set forth in the following Table II.

TABLE II

| Carbon Source | Final pH | Final Beer Viscosity (cps) | Yield % |
|---|---|---|---|
| 2% Starch 1% Sucrose | 5.5 | 4,700 | 1.85 |
| 2% Starch 1% Glucose | 7.3 | 25 | 1.60 |
| 2.5% Starch 0.5% Glucose | 6.5 | 2,800 | 1.81 |
| 3% Starch | 5.25 | 5,200 | 1.50 |

As illustrated in the above Table, the use of hydrolyzed starch in combination with sucrose proved to be a satisfactory carbon source for the fermentation. However, the presence of glucose in the fermentation medium was found to have an inhibiting effect upon the ability of the bacteria to produce the heteropolysaccharide. In the above tests, the incubation time at 30° C. was 72 hours. Similar results are obtained with *Klebsiella pneumoniae* Fer-1, ATCC 31311.

EXAMPLE III

In still further experiments, conducted in the same manner as described in Example II, various other mixed carbon sources were employed to determine their efficiency in the production of the desired heteropolysaccharide. The results of these experiments are set forth in the following Table.

TABLE III

| Carbon Source | | Final pH | Final Beer Viscosity (cps) |
|---|---|---|---|
| 1.5% Starch | 1.5% Sucrose | 6.8 | 3,350 |
| 1.5% Dextrin-1 | 1.5% Sucrose | 6.5 | 600 |
| 1.5% Maltose | 1.5% Sucrose | 6.8 | 2,650 |
| 1.5% Maltose | 1.5% Dextrin-1 | 6.5 | 2,150 |
| 3% Starch | | 7.0 | 4,600 |

As illustrated, the *Klebsiella pneumoniae* in these experiments was able to utilize various mixed carbon sources in the production of the heteropolysaccharide. In all cases, however, the most efficient carbon source was hydrolyzed starch which had been previously treated with an α-amylase enzyme followed by treatment at high temperature in the manner described previously. Similar results are obtained with *Klebsiella pneumoniae* Fer-1, ATCC 31311.

EXAMPLE IV

The effect of various carbon sources on the fermentation with *Klebsiella pneumoniae* ATCC 21711 were studied in sterilized one gallon fermentors. The fermentors contained 2.5 liters of E-1 medium and 200 milliliters of a 24-hour seed grown in a basal E-1 medium and 300 milliliters of the carbon source—all being added aseptically. During the fermentation, the temperature was maintained at 30° C., and the fermentation mixture was continuously aerated and agitated. The fermentation time in the one-gallon fermentor was 48 hours and the results of the fermentation are shown in the following Table. Similar results are obtained with *Klebsiella pneumoniae* Fer-1, ATCC 31311.

TABLE IV

| Carbon Source | | Final pH | Final Beer Viscosity (cps) |
|---|---|---|---|
| 3% Starch | | 6.0 | 5,700 |
| 2.75% Starch | 0.25% Dextrin-2 | 5.9 | 5,900 |
| 2.50% Starch | 0.50% Dextrin-2 | 6.0 | 5,800 |
| 1.5% Starch | 1.5% Dextrin-2 | 6.2 | 3,250 |
| 2.75% Dextrin-2 | 0.25% Glucose | 6.7 | 500 |

TABLE IV-continued

| Carbon Source | | Final pH | Final Beer Viscosity (cps) |
|---|---|---|---|
| 2.90% Dextrin-2 | 0.10% Glucose | 6.9 | 700 |

As shown in the above Table, the use of a mixture of hydrolyzed starch with Dextrin-2 as the carbon source provided satisfactory fermentations as indicated by the final viscosities of the fermentation beer. However, the use of Dextrin-2 with glucose as the carbon source was found to be unsatisfactory as was indicated by the low viscosity of the fermentation beer.

EXAMPLE V

In a further series of experiments with *Klebsiella pneumoniae* ATCC 21711 conducted in the same manner as set forth in Example I, fermentations were carried out in shake flasks at 30° C. for 80 hours. The seed for the experiments was obtained by growing the bacteria for 24 hours in E-1 medium containing 3% by weight of hydrolyzed starch as the carbon source. The quantity of the seed inoculum was 1% by weight of the total weight of the fermentation medium. The carbon source employed in each of the experiments was varied to determine the effect of the degree of starch hydrolysis on the fermentation. The individual carbon sources were prepared by heating Pearl starch (Staley Manufacturing Company) at a concentration of 30% by weight in water with varying quantities of an α-amylase enzyme, (Tenase, supplied by Miles Laboratories). After addition of the α-amylase enzyme, the starch solution was incubated at 60° C. for 2 hours and then placed in a boiling water bath for 30 minutes or autoclaved for 15 minutes at 15 psi at a temperature of 120° C. The weight percent of the α-amylase enzyme used in the hydrolysis of the starch carbon source is set forth in the following Table, together with the final pH and the final viscosity of the fermentation medium.

TABLE V

| Percent Tenase/Starch (w/w × 100) | Final pH | Final Beer Viscosity (cps) |
|---|---|---|
| 0.22 | 7.3 | Close 0 |
|  | 7.3 | to 0 |
| 0.56 | 7.0 | 1,325 |
|  | 6.9 | 1,275 |
| 1.11 | 6.9 | 2,000 |
|  | 6.85 | 2,200 |
| 2.22 | 6.8 | 3,600 |
|  | 6.75 | 3,300 |

As demonstrated by the above data, when the starch was insufficiently hydrolyzed, the fermentation was unsatisfactory and essentially no product was obtained. As the degree of hydrolysis of the starch used as a carbon source was increased, there was obtained a corresponding increase in the efficiency of the fermentation and in the yield of the desired heteropolysaccharide.

The viscosities set forth in Examples I-V were obtained by the use of a Brookfield Viscometer at 60 rpm and a temperature of 25° C. using a No. 4 spindle. Similar results are obtained with *Klebsiella pneumoniae* Fer-1, ATCC 31311.

EXAMPLE VI

This fermentation was carried out in a 5-liter fermentor. *Klebsiella pneumoniae* ATCC 21711 seed was prepared in another 5-liter fermentor containing E-1 medium and 3% by weight of hydrolyzed starch as the carbon source. This seed was used at 48 hours growth to inoculate (6.7% inoculum size) a 5-liter fermentor containing a final volume of 3 liters of E-1 medium with 3% by weight of hydrolyzed starch (Dextrose Equivalent 22.5) as the carbon source. The aeration rate was one liter per minute. The agitation rate was set at a tip speed of 260 feet per minute and increased to a maximum of 780 feet per minute as necessary to ensure adequate mixing during the fermentation. The fermentation temperature was 30° C. By 64 hours the viscosity of the fermentation beer was 8900 cps. with a pH of 6.2. At this time the beer was treated with isopropanol at a ratio of about 4-5 parts alcohol to one part beer. The beer was added to the alcohol as the alcohol was being agitated vigorously with a Lightnin' mixer. The resulting precipitate of Heteropolysaccharide-10 was recovered by straining it from the fermentation liquor. It was pressed to remove excess fluid, and dried at about 100° C. for 12 hours. Substantially pure heteropolysaccharide is obtained as a pale cream-colored powder, (yield 1.85%). This heteropolysaccharide had a 1% reconstituted viscosity of 1700 cps, and is soluble in hot and cold water.

Although the product so obtained is highly pure, it is further purified, if desired, by dissolving in water and re-precipitating with isopropanol. It is recovered and dried as described previously.

The viscosities were measured at 25° C. using a Brookfield Viscometer at 60 rpm and a No. 4 spindle.

Heteropolysaccharide-10 is quite sensitive to shear. To determine the effects of shear, 1% by weight aqueous solutions of heteropolysaccharide were made up in distilled water. The shear rate was then varied from 0.84 to 8.4 reciprocal seconds, and the viscosity of the solution was measured using a Brookfield Synchro-Lectric Viscometer, Model LVF, using a No. 4 spindle at 60 rpm at a temperature of 25° C. The results of these tests are set forth in the following table.

TABLE VI

| Shear Rate (sec$^{-1}$) | Viscosity (cps) |
|---|---|
| 8.4 | 1800 |
| 4.2 | 2650 |
| 1.7 | 4000 |
| 0.84 | 6500 |

As shown by the above data, the viscosity of the test solutions were greatly increased as the shear rate was reduced. A reduction in the shear rate from 8.4 to 0.84 sec$^{-1}$ produced a viscosity increase from 1800 to 6500 cps.

In further tests, various solutions were made up by the addition of the milled Heteropolysaccharide-10 to 100 milliliters of distilled water. The heteropolysaccharide was then mixed into the distilled water with a Lightnin' mixer and the test samples were allowed to sit undisturbed for 15 minutes before their viscosity was measured. The viscosities were measured using a Brookfield Synchro-Lectric Viscometer, Model LVF, using a No. 4 spindle at 60 rpm and a temperature of 25° C. The results of these tests are set forth in the following Table:

TABLE VII

| Concentration of Heteropolysaccharide (wt %) | Viscosity (cps) |
|---|---|
| 0.2 | 0 |
| 0.4 | 25 |

TABLE VII-continued

| Concentration of Heteropolysaccharide (wt %) | Viscosity (cps) |
| --- | --- |
| 0.6 | 750 |
| 0.8 | 1350 |
| 1.0 | 1950 |
| 1.2 | 3150 |
| 1.4 | 4650 |
| 1.6 | 5900 |
| 1.8 | 7350 |

As illustrated by the above data, small incremental increases in the concentration of the heteropolysaccharide produced relatively large incremental increases in viscosity. When the data in Table VII is plotted in the form of a viscosity-concentration curve (with viscosities as ordinates and concentrations as abscissas), the slope of the curve is relatively steep as compared with the viscosity concentration curves of other thickeners. This demonstrates the superiority of the Heteropolysaccharide-10 as compared in general with other thickeners.

In further tests, aqueous solutions of our heteropolysaccharide were made up and their viscosities were measured at various temperatures. It was found that there was a viscosity loss as the temperature was increased and that the rate of viscosity loss was approximately 25 cps per °C. This thermal viscosity change was temperature reversible up to a temperature of about 92° C. maintained for about 15 minutes. Thus, when these conditions were not exceeded, there was a corresponding viscosity gain of approximately 25 cps per °C. as the temperature of the solution was decreased.

In further experiments, tests were carried out to determine the rapidity of viscosity recovery in an aqueous solution containing the heteropolysaccharide which had previously been subjected to shear forces. A 1% aqueous solution of the heteropolysaccharide was made up in distilled water and subjected to shear by mixing for 1 hour with a Lightnin' mixer. Following this, the solution was permitted to stand and the viscosity was measured at 20, 40, 60 and 120 minutes after the shear forces had been removed. The viscosity measurements were made with a Brookfield Synchro-Lectric Viscometer, Model LVF, at 60 rpm and 25° C. These results are shown in the following Table:

TABLE VIII

Recovery of Viscosity Lost Due to Shear

| Time After Shear (Minutes) | Viscosity (cps) | Percent Increase in Viscosity |
| --- | --- | --- |
| 20 | 1550 | — |
| 40 | 1700 | 9 |
| 60 | 1850 | 19 |
| 120 | 1900 | 23 |

As shown in the above Table, the viscosity of the solution built up gradually following the removal of the shear forces. However, the viscosity build-up was time dependent and did not occur instantaneously. The viscosity build-up was essentially complete after one hour since the viscosity had then almost returned to its original value.

In further tests which were conducted with the heteropolysaccharide, its stability was observed under varying pH conditions. The viscosity of aqueous solutions of the heteropolysaccharide was quite stable within a pH range of about 5 to about 10. At an acid pH of less than about 5, there was a drop in the viscosity of the solution which was, however, at least partially recoverable on the addition of base to increase the pH of the solution to about 5 or higher. At an alkaline pH in excess of about 10, there was a loss in the viscosity of the aqueous solution containing the heteropolysaccharide. This loss was a permanent one which could not be recovered by the addition of acid to lower the pH within the range of about 5 to about 10.

The stability of the heteropolysaccharide with respect to various salts was also studied. The salts included sodium chloride, potassium chloride, ammonium sulfate, zinc sulfate, calcium chloride, magnesium sulfate, aluminum nitrate, chromium nitrate and $Na_4B_4O_7 \cdot 10H_2O$. In general, the viscosity of an aqueous solution containing the heteropolysaccharide is decreased by the addition of salts. The viscosity loss resulting from the addition of the salts occurs on the addition of a relatively small amount of the salt, such as 0.1 to 0.2%. On the addition of a further quantity of salt, there is, in general, no further decrease in the viscosity of the aqueous solution.

The rheological properties of Heteropolysaccharide-10 are summarized in the following Table IX.

TABLE IX

| 1% by weight viscosity | 1,400 cps |
| --- | --- |
| 2% by weight viscosity | 7,800 cps |
| Yield Point | 6.6 dynes/cm.$^2$ |
| Shear Stress | 132 dynes/cm.$^2$ |
| 2% by weight Haake viscosity | 156,000 cps |
| Thixotropy | 1.08 |
| Pseudoplasticity | |
| Low degree (LDP) | 80 |
| High degree (HDP) | 172 |

In the above Table, the 1% and 2% viscosities were measured on a Brookfield Synchro-Lectric Viscometer Model LVF at 60 rpm with the No. 3 and No. 4 spindles, respectively. The remaining rheological data was obtained using a Haake Rotovisco-Dual 50/500 employing a model MV 1 cup and bob.

The shear stress is determined at 8.45 sec$^{-1}$. The shear stress (dynes cm$^{-2}$) is calculated by multiplying the reading obtained at 8.45 sec$^{-1}$ by 3.4. The yield point is determined by the following procedure: After obtaining a steady reading at 8.45 sec$^{-1}$, the gear is disengaged and the reading 60 seconds later is recorded. This reading times 3.4 is the yield point in dynes cm$^{-2}$.

The thixotrophy was obtained by measuring the shear stress at 8.45 sec$^{-1}$, then shearing the gum at 1370 sec$^{-1}$ followed by measuring the shear stress again at 8.45 sec$^{-1}$. The thixotrophy is then calculated as the ratio of the unsheared and sheared readings, respectively.

Pseudoplasticity is the log log slope of shear rate versus shear stress. The LDP is calculated using the formula $$\left( \frac{2.000}{\log B/A} - 1 \right) \times 100$$

where A is the shear stress at 0.0845 sec$^{-1}$ and B is the shear stress at 8.45 sec$^{-1}$. The 2.000 is the log of the ratio of shear rates. The HDP is calculated by the formula $$\left(\frac{2.210}{\log C/B} - 1\right) \times 100$$

where B is the shear stress at 8.45 sec$^{-1}$, C is the shear stress at 1370 sec$^{-1}$ and 2.210 is the log of the ratio of the two shear rates. The 2% Haake viscosity is taken using the MVI cup and bob and recording the reading at 0.0326 sec$^{-1}$. This viscosity (cps) is calculated by multiplying the reading times 11,632.

The compatibility of Heteropolysaccharide-10 with cationic dyes such as Methylene Blue-chloride was determined by preparing 100 grams of a distilled water solution containing 0.5 percent of the heteropolysaccharide. Aliquots of powdered methylene blue chloride were then added to the test solution and stirred in, after which the viscosity was measured at 25° C. using a Brookfield Synchro-Lectric Viscometer, Model LVF, with a No. 3 spindle at 60 rpm. The results of these experiments are shown in the following Table.

TABLE X

| mg. Methylene Blue added (accumulative) | Viscosity cps |
|---|---|
| 0 | 430 |
| 35 | 300 |
| 60 | 250 |
| 85 | 225 |
| 100 | 200 |
| 150 | 100 |
| 175 | 0 |

As demonstrated by the above data, the progressive addition of methylene blue chloride to the test solution caused a decrease in its viscosity. By progressively increasing the concentration of methylene blue chloride, the viscosity was decreased until it reached a viscosity of essentially 0 cps. The heteropolysaccharide was, however, compatible with the methylene blue chloride at all the concentration levels used in the experiments and was not precipitated by the methylene blue chloride.

Experiments were also conducted to determine the effect of pH on the viscosity of a solution containing methylene blue chloride and the heteropolysaccharide of our invention. In these experiments, volumes of glacial acetic acid were added to 100 ml of a 0.5% by weight aqueous solution of the heteropolysaccharide which contained one gram of methylene blue chloride. The results of these experiments are shown in Table XI.

TABLE XI

| Volume Acid Added (ml.) | pH | Viscosity (cps) |
|---|---|---|
| 1.1 | 3.35 | 0 |
| 1.3 | 3.20 | 0 |
| 1.4 | 3.20 | 0 |
| 1.45 | 3.20 | 25 |
| 1.50 | 3.15 | 45 |
| 1.55 | 3.15 | 55 |
| 1.60 | 3.12 | 60 |
| 1.70 | 3.10 | 80 |
| 1.80 | 3.10 | 80 |
| 2.00 | 3.00 | 85 |
| 2.20 | 3.00 | 90 |
| 2.50 | 3.00 | 100 |
| 3.00 | 2.95 | 100 |

As demonstrated by the above data, the viscosity of the test solution was restored to its normal viscosity (absent the methylene blue chloride) by the addition of the glacial acetic acid. At glacial acetic acid levels of less than 1.4 ml there was no increase in the viscosity of the system. However, as the level of glacial acetic acid was increased to levels of 1.5 ml and higher, there was an increase in viscosity. The viscosity continued to increase as the acid level was increased up to a total of 2.5 ml. When the level of glacial acetic acid was increased to more than 2.5 ml, no further increase in viscosity was observed.

In further experiments, a 1% by weight solution of the heteropolysaccharide containing 1% by weight of methylene blue chloride was treated by the slow addition of glacial acetic acid. It was found that the solution had essentially no viscosity until the pH reached a level of about 3.4–3.5. At lower pH levels the solution gained in viscosity.

When a small amount of sodium hydroxide was added, the viscosity decreased to essentially zero. This procedure could be repeated several times by first adding acid, then a base, etc., to produce increases and decreases in viscosity. When the pH of the solution was increased to about 4.4–4.6, this also produced an increase in the viscosity of the solution to essentially its original levels (as it would be without the presence of methylene blue chloride) and this viscosity change then became pH irreversible.

The above results indicated that the electrolyte concentration (e.g., the concentration of sodium acetate in the above experiments) is another important factor in determining the viscosity of a solution of the heteropolysaccharide in the presence of methylene blue chloride.

Experiments were conducted to determine the relationship between electrolyte concentration and pH on the viscosity of an aqueous solution of the Heteropolysaccharide-10 in the presence of methylene blue chloride. In these experiments, a 0.5% by weight solution of the heteropolysaccharide in distilled water was prepared.

Seven hundred ml. portions of the heteropolysaccharide solution were then adjusted to pHs of approximately 7.5, 6.0, 4.5, 3.9 and 3.1. These solutions were then divided into 100 ml samples and NaCl was added (in the form of a 30% by weight NaCl solution) to provide NaCl concentrations of 0, 0.5, 0.10, 0.15, 0.20 and 0.30% by weight. The test solutions were mixed and to each sample was added 200 mg. of methylene blue chloride. The viscosity in centipoises of each sample was then measured using a Brookfield Synchro-Lectric Viscometer, Model LVF, at 60 rpm and 25° C. using a No. 3 spindle. The data from these experiments are shown in the following Table XII.

TABLE XII

| (% by wt) NaCl Conc. | Approximate pH of Heteropolysaccharide Solutions | | | | | | | | | |
|---|---|---|---|---|---|---|---|---|---|---|
| | 7.5 | | 6.0 | | 4.5 | | 3.9 | | 3.1 | |
| | pH | Vis. | pH | Vis. | pH | Vis. | pH | Vis. | pH | Vis. |
| 0 | 7.4 | 0 | 5.75 | 0 | 4.2 | 0 | 3.75 | 25 | 3.1 | 110 |
| 0.05 | 7.4 | 40 | 5.9 | 30 | 4.4 | 80 | 3.7 | 75 | 3.1 | 115 |
| 0.10 | 7.5 | 130 | 6.0 | 110 | 4.4 | 130 | 3.9 | 125 | 3.1 | 115 |
| 0.15 | 7.5 | 180 | 6.0 | 175 | 4.4 | 160 | 3.95 | 140 | 3.2 | 115 |
| 0.20 | 7.5 | 190 | 6.0 | 185 | 4.35 | 170 | 3.95 | 150 | 3.2 | 115 |
| 0.30 | 7.5 | 190 | 5.95 | 180 | 4.4 | 170 | 3.95 | 150 | 3.1 | 110 |

As demonstrated by the above data, the loss in viscosity of the test solution resulting from the presence of methylene blue chloride could be regained merely by increasing the electrolyte concentration without altering the pH.

The relationship between the nature of the electrolyte and its concentration were studied in determining the functioning of the electrolyte in restoring the viscosity of a test solution containing Heteropolysaccharide-10 together with methylene blue chloride. In these experiments, a 0.5% by weight solution of the heteropolysaccharide was made up in distilled water. Two hundred milligrams of methylene blue chloride were added to 100 grams of the above solution and mixed by stirring until the viscosity of the solution had decreased to 5 cps. or less when measured with the No. 2 spindle at 60 R.P.M. on a Brookfield Synchro-Lectric Model LVF Viscometer. Following this, varying amounts of a sodium salt were added to aliquots of the heteropolysaccharide-methylene blue chloride solution. Varying amounts of a magnesium salt were also added to aliquots of the heteropolysaccharide-methylene blue chloride solution to determine the relative effect of the magnesium and sodium ion concentrations on the viscosity of the solution. After addition of salt to the solution, its viscosity was again measured with a Brookfield Synchro-Lectric Model LVF Viscometer. The results of these experiments are shown in the following Table in which the cation molarity is shown in column 1, while the resulting viscosity of the solution in centipoises is shown in column 2 for the addition of sodium ions and in column 3 for the addition of magnesium ions.

TABLE XIII

| Concentration of Cation (Molar) | Viscosity (cps) | |
|---|---|---|
| | Na$^+$ | Mg$^+$ |
| 0.004 | 2.5 | 10 |
| 0.008 | 8 | 50 |
| 0.012 | 19 | 73 |
| 0.016 | 45 | 85 |
| 0.020 | 65 | 92 |
| 0.024 | 80 | — |
| 0.026 | 85 | — |

As shown in the above table, divalent cations, e.g., magnesium, are considerably more effective than monovalent cations, e.g., sodium, in restoring the viscosity of a solution of heteropolysaccharide which contains methylene blue chloride. Both of the salts were added as concentrated solutions, i.e., a 4.35 Molar solution of NaCl and a 4.12 Molar solution of MgCl$_2$.6H$_2$O.

Further experiments were performed to determine the effect of various anions on the viscosity of a solution of our heteropolysaccharide which contained methylene blue chloride. A test solution was made up in the manner previously described with regard to Table XIII by adding 200 mg. of methylene blue chloride to 100 gms. of a 0.5 percent by weight solution of heteropolysaccharide in distilled water. To aliquots of the test solution were added MgCl$_2$.6H$_2$O, MgSO$_4$.7H$_2$O and Mg(NO$_3$)$_2$.6H$_2$O. The salts were added as crystals to the test solution and were mixed in by stirring. The results of these experiments are shown in the following Table XIV in which the molarity of the anion in the test solution is shown in column 1 and the resulting viscosity of the test solution is shown in columns 2–4 for the anions CL$^-$, NO$_3^-$ and SO$_4^=$. The viscosities were measured at about 25° C. and 60 R.P.M. using a Brookfield Synchro-Lectric Model LVF Viscometer.

TABLE XIV

| Anion Molarity | Viscosity (cps) | | |
|---|---|---|---|
| | Cl | NO$_3^-$ | SO$_4^=$ |
| 0.004 | 12 | 13 | 32 |
| 0.008 | 17.5 | 17.5 | 87.5 |
| 0.012 | 31 | 25 | 98 |
| 0.016 | 52.5 | 42.5 | 107.5 |
| 0.020 | 58 | 62 | — |
| 0.030 | 69 | 77 | — |

As demonstrated by the above data, the polyvalent anions, e.g., sulfate, are more effective than the monovalent anions such as chloride or nitrate in restoring the viscosity of the test solution. Thus, at the same molar concentration, the sulfate ion is more than twice as effective as the chloride or nitrate ion in terms of the resulting viscosity of the test solution in centipoises.

Still further experiments were conducted in which the combined presence of the cations and anions in a test solution were evaluated in terms of their effect in restoring the viscosity of a solution of our heteropolysaccharide containing methylene blue chloride. As in the experiments reported in Table XIV, methylene blue chloride was added to a 0.5 percent solution of heteropolysaccharide in distilled water to reduce its viscosity to 5 cps or less when measured with a Brookfield Synchro-Lectric Model LVF Viscometer. To aliquots of the test solution were added MgCl$_2$.6H$_2$O or MgSOhd 4.7H$_2$O in crystal form followed by mixing of the salts by stirring. Following this, the viscosities were measured with a Brookfield Synchro-Lectric Model LVF Viscometer. The data from these experiments is reported in Table XV in which the ionic strength ($\mu$) is shown in column 1 and the viscosity in centipoises is shown in column 2 for MgCl$_2$.6H$_2$O and in column 3 for MgSO$_4$.7H$_2$O. The ionic strength ($\mu$) is determined from the formula: $\mu = \Sigma mz^2$ in which m is equal to the molarity of each ion in the salt and z is equal to the valence of each ion of the salt. The ionic strength is thus equal to the summation of the mz$^2$ values for each ion in the salt.

TABLE XV

| (ionic strength) | Viscosity (cps) | |
|---|---|---|
| | $MgCl_2 \cdot 6H_2O$ | $MgSO_4 \cdot 7H_2O$ |
| 0.008 | 13 | 16 |
| 0.016 | 33 | 33 |
| 0.024 | 65 | 65 |
| 0.032 | 80 | 95 |
| 0.040 | 85 | 108 |
| 0.048 | 90 | 117.5 |
| 0.056 | 93 | 123 |

From an analysis of the above data, it can be seen that there is a correlation between the ionic strength of the added salt and the resulting viscosity. Compare, for example, the results of Table XV with those of Table XIV. The anions, $Cl^-$ and $SO_4^=$, in Table XIV were added in the form of $MgCl_2.6H_2O$ and $MgSO_4.7H_2O$ salts—the same salts as added in Table XV. By expressing the results in terms of ionic strength ($\mu$) in Table XV, a correlation (though not 100% exact) is observed between the salts $MgCl_2.6H_2O$ and $MgSO_4.7H_2O$ in restoring the viscosity of the test solution. However, when the data are expressed merely in terms of the anion concentration, as in Table XIV, no correlation is evident between the $Cl^-$ and $SO_4^=$ ions—except that the $SO_4^=$ ion is much more effective at the same molarity.

The compatibility of Heteropolysaccharide-10 with cationic materials such as Methylene Blue chloride makes it useful as a thickener in applications which utilize cationic materials. Thus, for example, it may be used as a print paste thickener for textile printing.

EXAMPLE VII

| Interior Premium Semi-Gloss Acrylic White Enamel | | |
|---|---|---|
| Materials | Pounds | Gallons |
| Water | 72.5 | 8.70 |
| Preservative (Dowicil 75) | 2.0 | 0.17 |
| Dispersant (Tamol 731) | 9.0 | 1.00 |
| Propylene glycol | 60.0 | 7.00 |
| Ethylene glycol | 22.0 | 2.25 |
| Carbitol Solvent | 18.0 | 2.25 |
| Surfactant (Aerosol OT, 75% aq) | 2.0 | 0.50 |
| Defoamer (Drew L455A) | 1.0 | 0.25 |
| Pigment (Tipure R-900) | 245.0 | 7.37 |
| Heteropolysaccharide-10 | 3.5 | 0.37 |
| Hexylene glycol | 10.0 | 1.31 |
| Acrylic resin (Rhoplex AC490) | 596.5 | 68.25 |
| Defoamer (Drew L455A) | 3.0 | 0.39 |
| Water | 16.7 | 2.00 |
| TOTAL | 1,044.5 | 102.19 |

The water, preservative, dispersant, propylene glycol, and ethylene glycol are charged to a mixing tank at low speed in order of listing. Carbitol Solvent is added while maintaining temperature below 130° F. The surfactant and first portion of defoamer are added at low speed. Then shift to high speed, add pigment and grind for 15–20 minutes. A premix made by adding the Heteropolysaccharide-10 to the hexylene glycol is added to the batch slowly at high speed mixing. The mixture is then ground at high speed for 30 minutes. After the grinding is completed, the mixture is added to a tank containing the acrylic resin and mixed at low speed. The balance of defoamer and water are added. Viscosity is adjusted if necessary by addition of up to about 1 gallon of a 1.5% solution of Heteropolysaccharide-10.

EXAMPLE VIII

Screen Printing Paste

A screen printing paste formulation for nylon carpet is prepared from the following formulation:

| Ingredient | Parts By Weight |
|---|---|
| Acid Blue 25 | 1.5 |
| Thiodiethylene glycol | 5.0 |
| Benzyl alcohol | 2.0 |
| Heteropolysaccharide-10 (2% stock solution) | 30.0 |
| Glacial acetic acid | 4.0 |
| Water | 57.5 |

The paste is printed on nylon carpet and fixed at atmospheric pressure using steam at 212°–215° F., followed by rinsing in cold water without any detergent, and drying.

EXAMPLE IX

Drilling Fluid

A drilling fluid for an oil field well is prepared from the following formulation:

| Heteropolysaccharide-10 | 0.14 |
|---|---|
| Water | 2.27 |
| KCl | 4.76 |

We claim:

1. A thickened aqueous composition that comprises an aqueous medium containing as a thickening agent from about 0.3% to about 3.0% by weight of Heteropolysaccharide-10, said heteropolysaccharide containing about 3% protein and about 97% carbohydrate, the carbohydrate portion of which contains about 19% of a uronic acid, about 39% glucose, about 29% galactose and about 13% fucose.

* * * * *